United States Patent
Serbousek et al.

(10) Patent No.: US 6,610,097 B2
(45) Date of Patent: Aug. 26, 2003

(54) PROSTHETIC CUP ASSEMBLY WHICH INCLUDES COMPONENTS POSSESSING SELF-LOCKING TAPER AND ASSOCIATED METHOD

(75) Inventors: Jon C. Serbousek, Winona Lake, IN (US); Frank S. Bono, Warsaw, IA (US); Stacey A. Trick, North Manchester, IN (US); Duane G. Snyder, Scottsdale, AZ (US); James G. Lancaster, Warsaw, IN (US)

(73) Assignee: DePuy Orthopaedics, Inc., Warsaw, IN (US)

( * ) Notice: Subject to any disclaimer, the term of this patent is extended or adjusted under 35 U.S.C. 154(b) by 0 days.

(21) Appl. No.: 10/056,910

(22) Filed: Jan. 25, 2002

(65) Prior Publication Data

US 2002/0068980 A1 Jun. 6, 2002

Related U.S. Application Data

(63) Continuation of application No. 09/525,791, filed on Mar. 15, 2000.

(51) Int. Cl.$^7$ .................................................. A61F 2/32
(52) U.S. Cl. ................................. 623/22.24; 623/22.28
(58) Field of Search ........................... 623/18.11, 19.11, 623/19.12, 20.11, 20.22, 22.11, 22.21, 22.24, 22.25, 22.28, 22.17, 22.18, 22.19, 22.2

(56) References Cited

U.S. PATENT DOCUMENTS

| | | |
|---|---|---|
| 2,910,978 A | 11/1959 | Urist |
| 3,584,318 A | 6/1971 | Scales et al. |
| 3,744,061 A | 7/1973 | Frost |
| 3,806,960 A | 4/1974 | Weber |
| 3,829,904 A | 8/1974 | Ling et al. |
| 4,031,570 A | 6/1977 | Frey |
| 4,596,580 A | 6/1986 | Weill |
| 4,650,491 A | 3/1987 | Parchinski |
| 4,678,472 A | 7/1987 | Noiles |
| 4,681,589 A | 7/1987 | Tronzo |
| 4,695,282 A | 9/1987 | Forte et al. |
| 4,704,127 A | 11/1987 | Averill et al. |
| 4,718,911 A | 1/1988 | Kenna |
| 4,784,663 A | 11/1988 | Kenna |

(List continued on next page.)

FOREIGN PATENT DOCUMENTS

| | | |
|---|---|---|
| DE | 196 16 059 A1 | 10/1997 |
| EP | 0 137 664 A2 | 8/1984 |
| EP | 0 214 885 A1 | 7/1986 |
| EP | 0 302 850 B1 | 7/1988 |
| EP | 0 315 795 A1 | 10/1988 |
| EP | 0 648 478 A2 | 4/1995 |
| EP | 0 773 007 A1 | 5/1997 |
| WO | WO 95/22944 | 8/1995 |
| WO | WO 95/23566 | 9/1995 |
| WO | WO 96/04862 | 2/1996 |
| WO | WO 96/04866 | 2/1996 |
| WO | WO 96/04867 | 2/1996 |
| WO | WO 96/23457 | 8/1996 |

OTHER PUBLICATIONS

H. Henning Freden, "Tapers, Spindle Noses, and Arbors", *Tool Engineer's Handbook*, pp. 1848–1860.

P.A. Dearnley, "A Review of Metallic, Ceramic and Surface–Treated Metals Used for Bearing Surfaces in Human Joint Replacements", Proc. Instn. Mech. Engrs., vol. 213, Part H, pp. 107–135.

*Primary Examiner*—David J. Isabella
(74) *Attorney, Agent, or Firm*—Maginot, Moore & Bowman (57) ABSTRACT

A prosthetic device, such as an acetabular cup, includes a shell, a liner and a bearing. The bearing may be coupled to the liner so as to form a bearing-liner subassembly. The shell is provided with a female taper complimentary to a male taper on the liner. The liner-bearing subassembly may be secured to the shell by engaging the complimentary tapers.

15 Claims, 9 Drawing Sheets

U.S. PATENT DOCUMENTS

| | | |
|---|---|---|
| 4,795,470 A | 1/1989 | Goymann et al. |
| 4,883,491 A | 11/1989 | Mallory et al. |
| 4,892,549 A | 1/1990 | Figgie, III et al. |
| 4,936,861 A | 6/1990 | Muller et al. |
| 4,978,356 A | 12/1990 | Noiles |
| 5,002,577 A | 3/1991 | Bolesky et al. |
| 5,019,105 A | 5/1991 | Wiley |
| 5,049,158 A | 9/1991 | Engelhardt et al. |
| 5,080,677 A | 1/1992 | Shelley |
| 5,108,445 A | 4/1992 | Ashby |
| 5,171,285 A | 12/1992 | Broderick |
| 5,222,984 A | 6/1993 | Forte |
| 5,226,917 A | 7/1993 | Schryver |
| 5,282,864 A | 2/1994 | Noiles et al. |
| 5,310,408 A | 5/1994 | Schryver et al. |
| 5,358,532 A | 10/1994 | Evans et al. |
| 5,383,938 A | 1/1995 | Rohr et al. |
| 5,413,603 A | 5/1995 | Noiles et al. |
| 5,443,519 A | 8/1995 | Averill et al. |
| 5,507,824 A | 4/1996 | Lennox |
| 5,549,698 A | 8/1996 | Averill et al. |
| 5,571,198 A | 11/1996 | Drucker et al. |
| 5,571,201 A | 11/1996 | Averill et al. |
| 5,577,368 A | 11/1996 | Hamilton et al. |
| 5,641,323 A | 6/1997 | Caldarise |
| 5,645,601 A | 7/1997 | Pope et al. |
| 5,645,606 A | 7/1997 | Oehy et al. |
| 5,658,294 A | 8/1997 | Sederholm |
| 5,658,346 A | 8/1997 | Willi |
| 5,658,347 A | 8/1997 | Sarkisian et al. |
| 5,658,348 A | 8/1997 | Rohr, Jr. |
| 5,676,704 A | 10/1997 | Reis et al. |
| 5,702,456 A | 12/1997 | Pienkowski |
| 5,702,476 A | 12/1997 | Limacher et al. |
| 5,702,477 A | 12/1997 | Capello et al. |
| 5,702,478 A | 12/1997 | Tornier |
| 5,702,483 A | 12/1997 | Kwong |
| 5,711,973 A | 1/1998 | Rothschild et al. |
| 5,725,589 A | 3/1998 | Pfaff et al. |
| 5,755,803 A | 5/1998 | Haines et al. |
| 5,755,808 A | 5/1998 | DeCarlo et al. |
| 5,756,027 A | 5/1998 | Rothschild et al. |
| 5,782,928 A | 7/1998 | Reis et al. |
| 5,782,929 A | 7/1998 | Sederholm |
| 5,782,930 A | 7/1998 | Lin et al. |
| 5,788,916 A | 8/1998 | Caldaries |
| 5,871,547 A | 2/1999 | Abouaf et al. |
| 5,879,402 A | 3/1999 | Lawes et al. |
| 5,879,404 A | 3/1999 | Bateman et al. |
| 5,879,405 A | 3/1999 | Reis et al. |
| 5,879,406 A | 3/1999 | Lilley |
| 5,879,407 A | 3/1999 | Waggener |
| 5,888,204 A | 3/1999 | Ralph et al. |
| 5,888,205 A | 3/1999 | Pratt et al. |
| 5,935,175 A | 8/1999 | Ostiguy, Jr. et al. |
| 6,129,765 A | 10/2000 | Lopez et al. |

PROSTHETIC CUP ASSEMBLY WHICH INCLUDES COMPONENTS POSSESSING SELF-LOCKING TAPER AND ASSOCIATED METHOD

This application is a continuation of co-pending U.S. patent application Ser. No. 09/525,791, filed on Mar. 15, 2000.

BACKGROUND AND SUMMARY OF THE INVENTION

This present invention is directed to a prosthetic cup assembly which is disclosed in the context of a hip prosthesis.

It is known to provide an acetabular cup assembly that includes a metal shell component for attachment to an acetabulum to replace the natural socket and a plastic bearing component that is inserted into the shell to provide a bearing surface for receiving a femur ball prosthesis element. See for example, U.S. Pat. No. 5,049,158, to John A. Englehardt et al., the disclosure of which is expressly incorporated herein by reference. In addition, traditional bearing components include a built-up lip around a portion of the bearing surface. See for example, U.S. Pat. Nos. 5,282,864 and 5,413,603 to Noiles et al., the disclosures of which are also expressly incorporated herein by reference According to the present invention a prosthetic cup assembly for use in a joint such as a hip joint is provided. The prosthetic cup assembly comprises a shell with a concave inner surface and a liner that is taper mounted to the inner surface of the shell. The cup assembly also includes a separate bearing securely attached inside the liner. Specifically, the inner surface of the shell provides, at its outer extent, a female taper opening into the shell. A male taper positioned on an outside surface of the liner engages the female taper to hold the bearing in the cup-like shell.

In another embodiment of the present invention, a kit is provided for the replacement of a cup portion of a bone of a joint. The kit comprises a shell formed with a concave inner surface providing, at its outer extent a female taper, and at least two bearing/liner subassemblies. The subassemblies include a bearing component mounted within a liner. The bearing component provides an internal cavity for receiving a ball and an opposite exterior coupled to an inside surface of the liner. The liner also has an outer surface providing a male taper sized for receipt by the female taper. The engagement of the female taper on the male taper provides the mechanical connection between the shell and the subassembly.

In yet another embodiment of the present invention, a method is provided for assembling a bearing/liner subassembly for a ball-joint type prosthetic appliance. The method includes the steps of cooling a bearing component that has an exterior with a normal pre-determined radius at a temperature sufficient to shrink the radius of the exterior and placing the cooled bearing component into a liner to form a bearing/liner subassembly. The liner has an inside surface facing the bearing component and an outer surface providing a male taper. The inside surface of the liner has a radius that is greater in size than the reduced radius of the bearing component and less than the normal pre-determined radius of the bearing component. Next, the subassembly is warmed to a temperature sufficient to return the exterior of the bearing component to the normal pre-determined radius. Thus, the bearing component is mounted in a fixed and locked position within the liner. The subassembly is then inserted into a shell that is formed with a generally hemispherical concave inner surface providing, at its outer extent a female taper for receiving the male taper of the liner. The engagement of the female taper on the male taper provides the mechanical connection between the shell and the liner.

In still another embodiment of the present invention, a prosthetic component assembly is provided for use in fixation to bone. The assembly includes a prosthetic component assembly for use in fixation to bone, the assembly comprising a shell formed with an inner surface providing at its outer extent a female taper, a liner formed with an inner end, an opposite outer end, an inside surface and an opposite outside surface extending between the inner and outer ends, a male taper positioned to lie on the outside surface adjacent the outer end for receipt by the female taper, the engagement of the female taper on the male taper providing a mechanical connection between the shell and the liner, and a bearing component. The bearing component is formed for coupling with the liner and has an internal cavity and an opposite exterior, the exterior being formed for engagement with the inner surface of the liner.

In a further embodiment of the present invention, a prosthetic cup assembly for use in fixation to bone is provided. The assembly includes a shell defining a shell cavity, the shell being configured with (i) an inner surface having a female taper, and (ii) a locking recess defined in the inner surface of the shell. The assembly further includes a bearing defining a bearing cavity adapted to receive a prosthetic ball therein, the bearing is configured with (i) an outer surface having a male taper, and (ii) a locking member extending outwardly from the outer surface of the bearing. When the bearing is positioned within the shell cavity, the male taper and the female taper engage each other so as to provide a first connection between the bearing and the shell. Further when the bearing is positioned within the shell cavity, the locking member is located within the locking recess so as to provide a second connection between the bearing and the shell.

Additional features of the present invention will become apparent to those skilled in the art upon consideration of the following detailed description of preferred embodiments exemplifying the best mode of carrying out the invention as presently perceived.

DETAILED DESCRIPTION OF THE DRAWINGS

Figure 1:
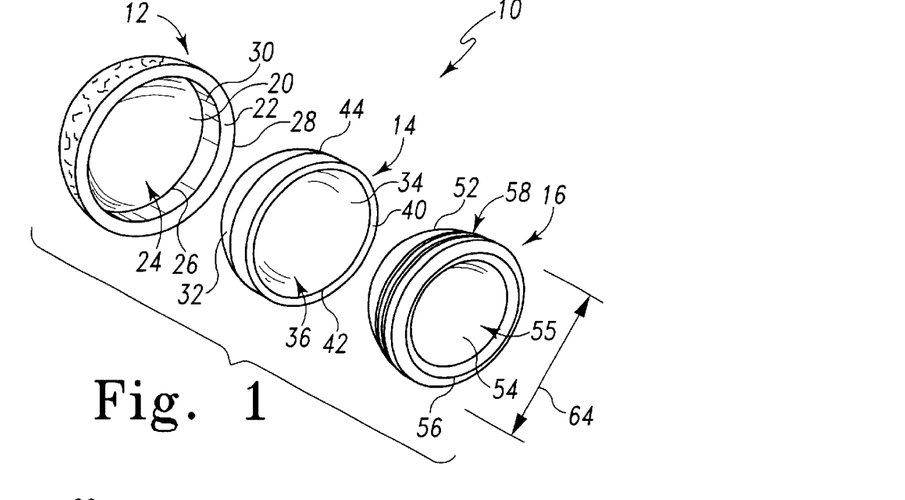
FIG. 1 is an exploded perspective view of an acetabular cup assembly according to one embodiment of the present invention.

An acetabular cup assembly 10 according to one embodiment of the present invention is shown in FIG. 1. Cup assembly 10 includes a shell 12 adapted to be affixed to the acetabulum (not shown) to replace the natural hip socket, a liner 14 adapted to be coupled to shell 12, and a bearing 16 adapted to be coupled to liner 14. Shell 12 includes an outer surface 18 that can be textured to facilitate securing shell 12 in place within an appropriately prepared acetabulum. Shell 12 is preferably made from titanium, but may be made from a cobalt chrome material or other suitable materials. Shell 12 also includes a generally hemispherical shaped inner surface 20. In this specification and in the claims, the words "generally hemispherical" are intended to cover the hemispherical ranges conventionally used in acetabular and glenoid shells, liners, and cup bearings including less than hemispherical and, in some cases, more than hemispherical. Shell 12 further includes a rim 22. Rim 22 defines a plane through which liner 14 and bearing 16 enter a cavity 24 of shell 12 formed by inner surface 20. Inner surface 20 of shell 12 is formed to include a side wall 26 providing, at its outer extent 28 a female taper 30. Female taper 30 extends around the entire periphery of cavity 24 adjacent rim 22. It is understood that the axial depth of female taper 30 within cavity 24 may vary.

Liner 14 includes an outside spherical surface 32 having a male taper 44 that is sized to engage and lock with female taper 30. It is understood that the length of male taper 44 may vary, so long as it securely engages female taper 30. Liner 14 is preferably made from titanium, but may be made from a cobalt chrome material, or other suitable materials. Liner 14 includes an inside surface 34 that preferably defines a chamber 36 sized for receiving bearing component 16.

Typically, inside surface 34 is generally hemispherical in shape. In addition, projections 53 may extend from inside surface 34 in a spaced-apart relationship relative to one another for secure engagement with bearing component 16. See FIG. 2. Typically, liner 14 includes four projections 53 positioned at approximately 90" relative to one another to prevent rotation of bearing component 16 within chamber 36. Liner 14 further includes an outer rim 40. Preferably, a locking tab 42 extends into chamber 36 from inside surface 34 adjacent outer rim 40. See FIG. 2.

Referring again to FIG. 1, bearing 16 includes an outer surface 52 that is generally hemispherical in shape. Bearing 16 also includes an inner bearing surface 54 that defines an opening 55 sized to receive a prosthetic femoral ball (not shown). A rim 56 extends circumferentially around opening 55 of bearing 16. Bearing 16 is symmetrical. It is understood, however, that bearing 16 of the present invention may be a nonsymmetrical component. Bearing 16 further includes a circumferential groove 58 spaced apart from rim 56 and sized to receive locking tab 42 of liner 14. Bearing 16 is preferably made from a polymeric material such as ultra high molecular weight polyethylene (UHMWPE). Of course, bearing 16 could be made of other types of implantable bearing materials such as a metal material or a ceramic material.

Figures 2, 3, 4:
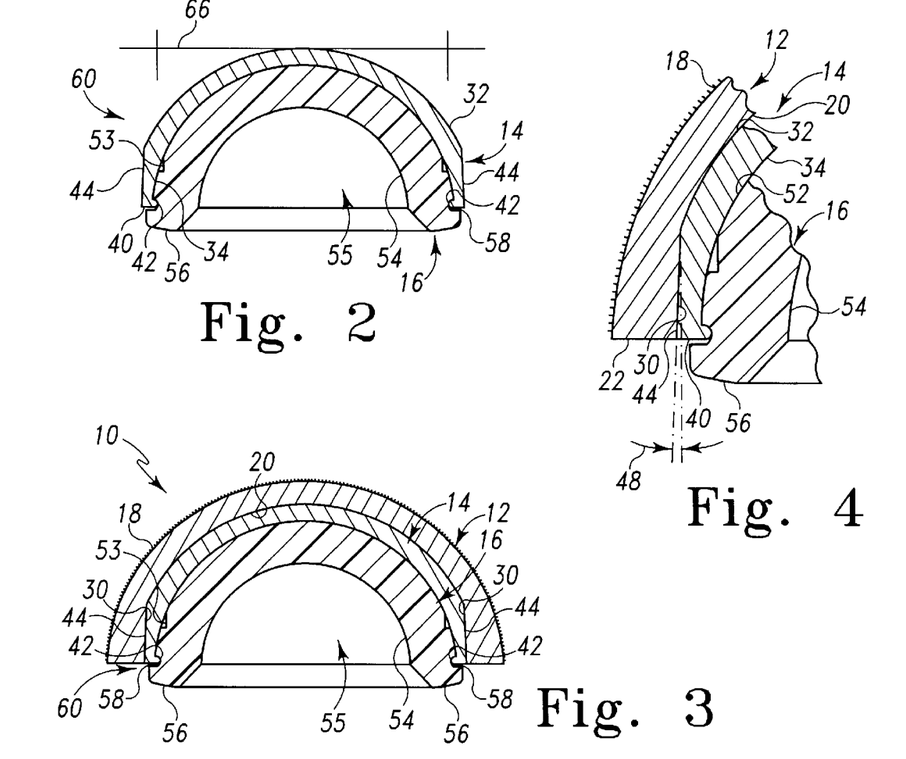
FIG. 2 is a cross-sectional view of the liner and bearing component of the acetabular cup assembly of FIG. 1 showing the bearing component mounted within the liner.
FIG. 3 is a cross-sectional view of the assembled acetabular cup assembly of FIG. 1.
FIG. 4 is an enlarged cross-sectional view of a portion of the acetabular cup assembly of FIG. 2.

As shown for example in FIG. 2 bearing 16 may be selectively coupled to liner 14 to form a subassembly 60 in accordance with a kit of the present invention. The user will receive the kit that includes shell 12, and at least two bearing/liner subassemblies 60, 160, 260 such as, for example of the types shown in FIGS. 2, 5 and 6 respectively. Once the user has affixed shell 12 to an appropriately prepared acetabulum, appropriate subassembly 60, 160, 260 for use with the environment may be selected.

Referring now to FIG. 2, to form subassembly 60 of the kit of the present invention, bearing 16 is press-fit into chamber 36 of liner 14. Inside surface 34 of liner 14 has an inner radius 66 that is less than a normal predetermined radius 64 (FIG. 1) of outer surface 52 of bearing 16. Therefore, prior to assembly, bearing 16 is cooled to a temperature that causes its outer surface 52, to shrink in size to a reduced second radius (not shown). It is understood that the amount of size reduction will vary depending upon the material used to construct bearing component 16 and the temperature to which bearing 16 is cooled. Typically, bearing 16 is cooled in liquid nitrogen, however other common refrigeration methods may be used. Therefore, once normal pre-determined radius 64 of outer surface 52 has been reduced, bearing 16 is press-fit into chamber 36 of liner 14. Circumferential groove 58 is generally aligned with locking tab 42 of liner 14. After circumferential groove 58 and locking tab 42 are aligned, bearing 16 is warmed to a temperature sufficient to return outside surface 52 of bearing 16 to a size approaching its normal pre-determined radius 64. Thus, bearing 16 and liner 14 are fastened together in a fixed and locked position and form bearing/liner subassembly 60.

This subassembly 60 is then inserted into cavity 24 of shell 12 to form assembled acetabular cup assembly 10. See FIG. 3. Once liner 14 is pressed into cavity 24, female and male tapers 30, 44 cooperate to hold subassembly 60 in place. Male taper 44 of liner 14 engages female taper 30 of shell 12 and forms a metal-to-metal locking mechanical connection therebetween. Tapers 30, 44 may be a straight taper, as in FIGS. 2–7, or they may be as a curve of a conic section—circle, ellipse, parabola, hyperbola or the like. If taper 44 of outside surface 32 of liner 14 is straight, taper 30 of side wall 26 of shell 12 is also straight.

Referring now to FIG. 4, tapers 30, 44 are machine tapers that provide a connection that ensures and maintains accurate alignment between shell 12 and liner 14 and permits shell 12 and liner 14 to be separated for reconditioning or for substitution of other parts. Tapers 30, 44 may be a self-holding taper (i.e. self-locking) or a self-releasing taper. Throughout the specification and claims the terms "self-holding" and "self-locking" are defined as male and female tapers that when in engagement with one another, tend to stay in place owing to the taper angle; no other means of holding is required. That is, in the case of straight, symmetric tapers, the included angle between diametrically opposite points on male taper 44 will be greater than zero degrees and less than or equal to about seventeen degrees. As shown in FIG. 4, which illustrates symmetrical tapers 30, 44, an angle 48 between the opposite points on male taper 44 is greater than zero degrees and less than or equal to about seven degrees. A curved locking taper is achieved when the acute angles between tangents to the curve over much of its length and perpendicular to rim 40 are greater than zero degrees and do not exceed about seven degrees. Removal of the male taper from the female taper is accomplished by starting the removal with a drift key or some other positive mechanism.

As used throughout the specification and claims, the term "self-releasing" is distinguished from the term "self-holding" (or "self-locking") by the taper angle that is sufficiently large to make retention of the male taper in the female taper dependent upon a positive locking device, such as the positive pressure from a corresponding femur head against bearing component 16. In the case of straight, symmetric tapers, the included angle between diametrically opposite points on male taper 44 will be about seventeen degrees. The taper fit between male and female tapers 30, 44 serves only to maintain alignment. Self-releasing tapers will release themselves.

Figure 5:
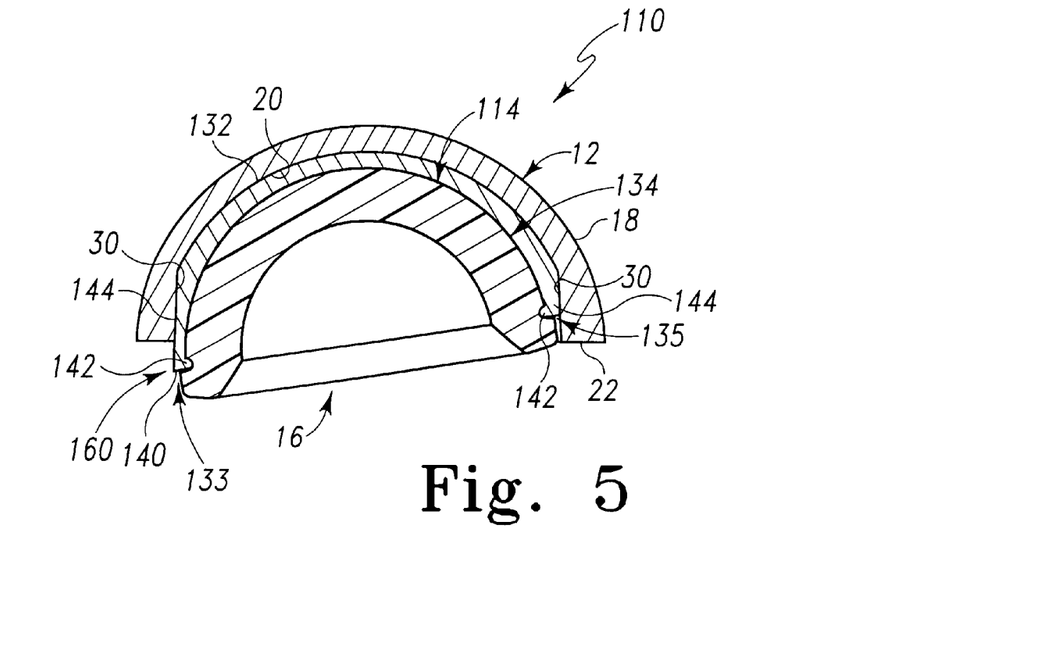
FIG. 5 is a cross-sectional view of an alternative embodiment of an acetabular cup assembly according to the present invention.

An alternative embodiment of acetabular cup assembly 110 is illustrated in FIG. 5. Acetabular cup assembly 110 includes shell 12, a liner 114 that is coupled in shell 12, and bearing 16 coupled to liner 114 to create liner/bearing subassembly 160. Liner 114 includes an outside surface 132 that is formed for engaging inner surface 20 of shell 12, an inside chamber 134, and an outer rim 140 extending about the circumference of liner 114. In addition, a locking tab 142 extends into inside chamber 134 for engagement with bearing 16. As shown in FIG. 5, outside surface 132 includes a male taper 144 that is angled about its circumference to create unequal tapering lengths on opposite sides 133, 135 of liner 114. This angled taper 144 causes liner/bearing subassembly 160 to be positioned in a lipped orientation within shell 12. It is understood that the angle can be varied to create various tapering lengths in order to create multiple orientations for subassembly 160 within shell 12. Such a lipped orientation can be beneficial in certain environments to aid in the prevention of femoral ball dislocation.

Figure 6:
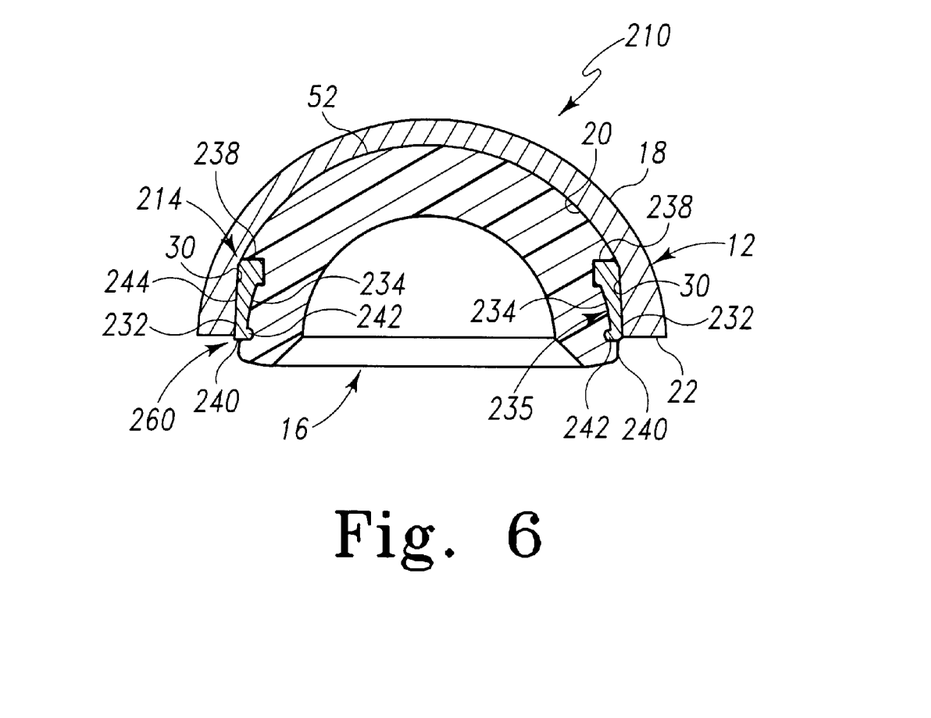
FIG. 6 is a cross-sectional view of an alternative embodiment of an acetabular cup assembly according to the present invention.

Yet another alternative embodiment of acetabular cup assembly 210 is illustrated in FIG. 6. Acetabular cup 210 includes shell 12, a liner 214 that is coupled in shell 12, and bearing 16 coupled to liner 214 to create liner/bearing subassembly 260. Liner 214 is ring-shaped and includes an outside surface 232 that is formed for engaging female taper 30 of shell 12 and an opposite inside surface 234. In addition, liner 214 includes an inner rim 238, an outer rim 240, and an inside chamber 235 extending between rims 238, 240. In addition, a locking tab 242 extends into inside chamber 235 for engagement with outside surface 52 of bearing 16. As shown in FIG. 6, outside surface 232 is formed as a male taper 244 that extends about the circumference. Thus, liner/bearing subassembly 260 when coupled within shell 12 positions bearing 16 within shell 12.

The taper feature of the present invention provides mechanical lock integrity for the two or three piece construct. This alternative design avoids the need for a metal locking ring and provides a rigid engagement of the liner, essentially eliminating the potential for any relative motion between the metal liner and the metal shell. Without this relative motion, the potential for abrasive wear on an outer surface of the bearing is substantially eliminated. Moreover, a liner that includes a tapered portion helps push the bearing into a pre-determined position and inhibits wear debris from escaping from the liner into the patient.

Additionally, the taper feature of the present invention may be applied to a wide variety of metal liner/plastic bearing subassemblies to create an infinite selection of bearing configurations within the metal shell. This feature is quite advantageous for surgeons who must select a proper configuration of the bearing component relative to a femur head during a surgical procedure. Preferably, each subassembly is infinitely adjustable within the shell to create a variety of orientations suitable for preventing dislocation of the corresponding femur head. Thus, the surgeon must only select a suitable bearing orientation relative to the femur head and press the subassembly in place to engage the corresponding tapers. Once the tapers are engaged, the acetabular cup assembly is automatically and easily held in place.

In addition, FIGS. 7–15 show still another embodiment of the present invention. In particular, FIGS. 7–9 disclose a shell 300 and FIGS. 10–15 disclose a bearing 302 which, when assembled together, collectively creates another acetabular cup assembly which incorporates the features of the present invention therein. The acetabular cup assembly which is made up of the components shown in FIGS. 7–15 is assembled by inserting the bearing 302 (see FIGS. 10–15) into a cavity 304 defined by the shell 300 in a manner similar to the insertion of the liner/bearing subassembly into the cavity of the shell as described above with respect to the embodiments depicted in FIGS. 1–6. However, it should be noted that the embodiment described with respect to FIGS. 7–15 is a two-piece cup assembly, while each of the embodiments described with respect to FIGS. 1–6 is a three-piece cup assembly.

Figure 7:
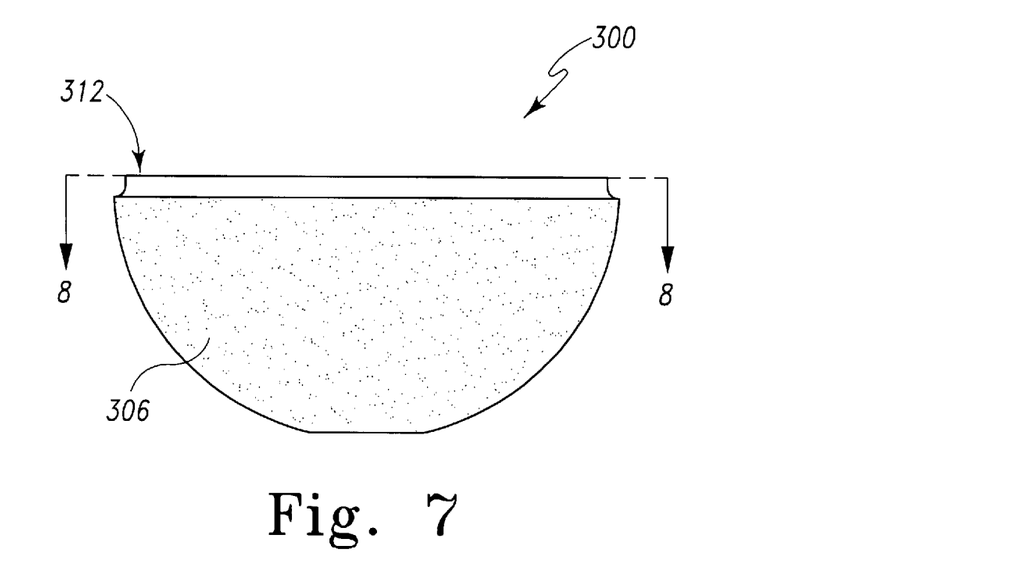
FIG. 7 is an elevational view of a shell which may be assembled with the bearing of FIGS. 10–15 or FIGS. 16–19 to create another acetabular cup assembly which incorporates the features of the present invention therein.

The shell 300 possesses a generally hemispherical shape and is preferably made from a metallic material such as a titanium alloy. Alternatively, the shell 300 may be made from a metallic material such as cobalt chrome. The shell 300 possesses a porous coating 306 located on an outer surface of the shell as shown in FIG. 7. The porous coating 306 is configured to facilitate biological ingrowth of a patient's bone within the outer surface of the shell whereby long-term fixation of the shell 300 to the patient's bone may be achieved. A number of spikes (not shown) may be secured to the outer surface of the shell to further facilitate fixation of the shell 300 to the patient's bone as is well known in the art. An apex hole 308 is defined in the shell 300. The apex hole is provided with a number of threads so as to allow coupling of an insertion instrument (not shown) thereto. The instrument may be coupled to the shell 300 during implantation of the acetabular cup assembly into the patient's body.

Figure 8:
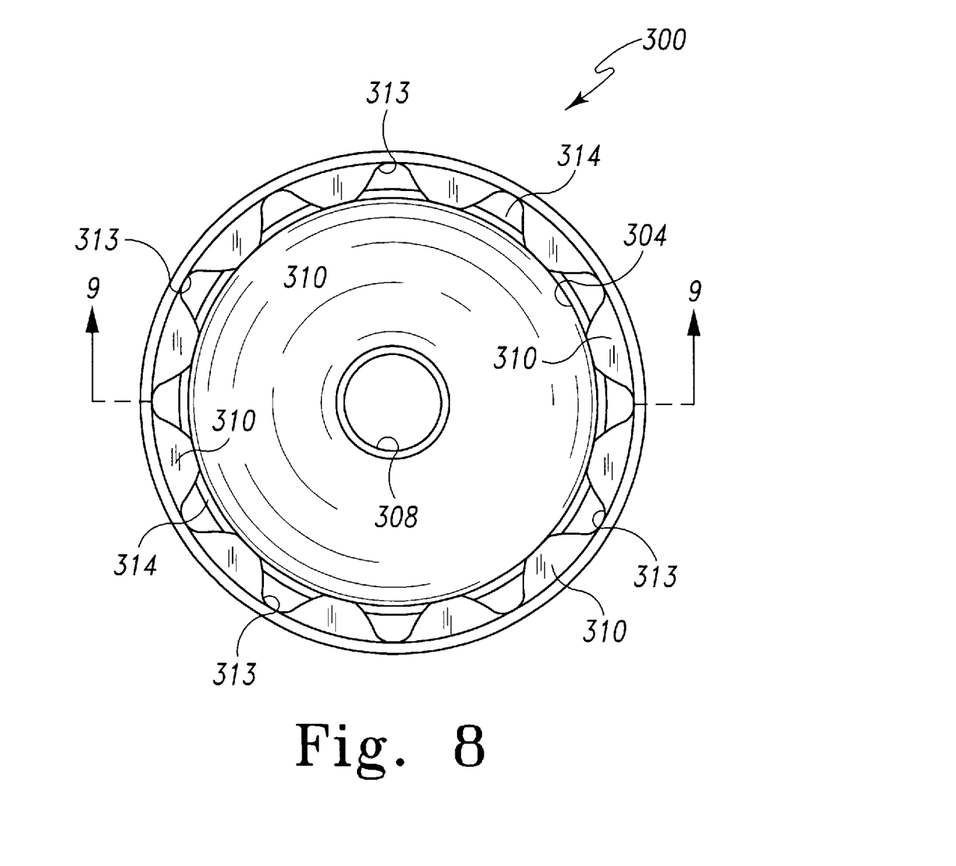
FIG. 8 is an elevational view of the shell of FIG. 7 as viewed in the direction of the arrows 8—8 of FIG. 7.

The shell 300 possesses a plurality of tangs 310 located at an upper rim 312 of the shell 300. Each of the plurality of tangs 310 extends inwardly toward the center of the shell 300 as shown in FIG. 8. The plurality of tangs 310 define a plurality of anti-rotation recesses 313 which are evenly spaced around the upper rim 312 of the shell 300 as shown in FIG. 8. The shell 300 also includes an annular recess 314 which is positioned immediately below the plurality of tangs 310 (see FIGS. 8 and 9).

Figure 9:
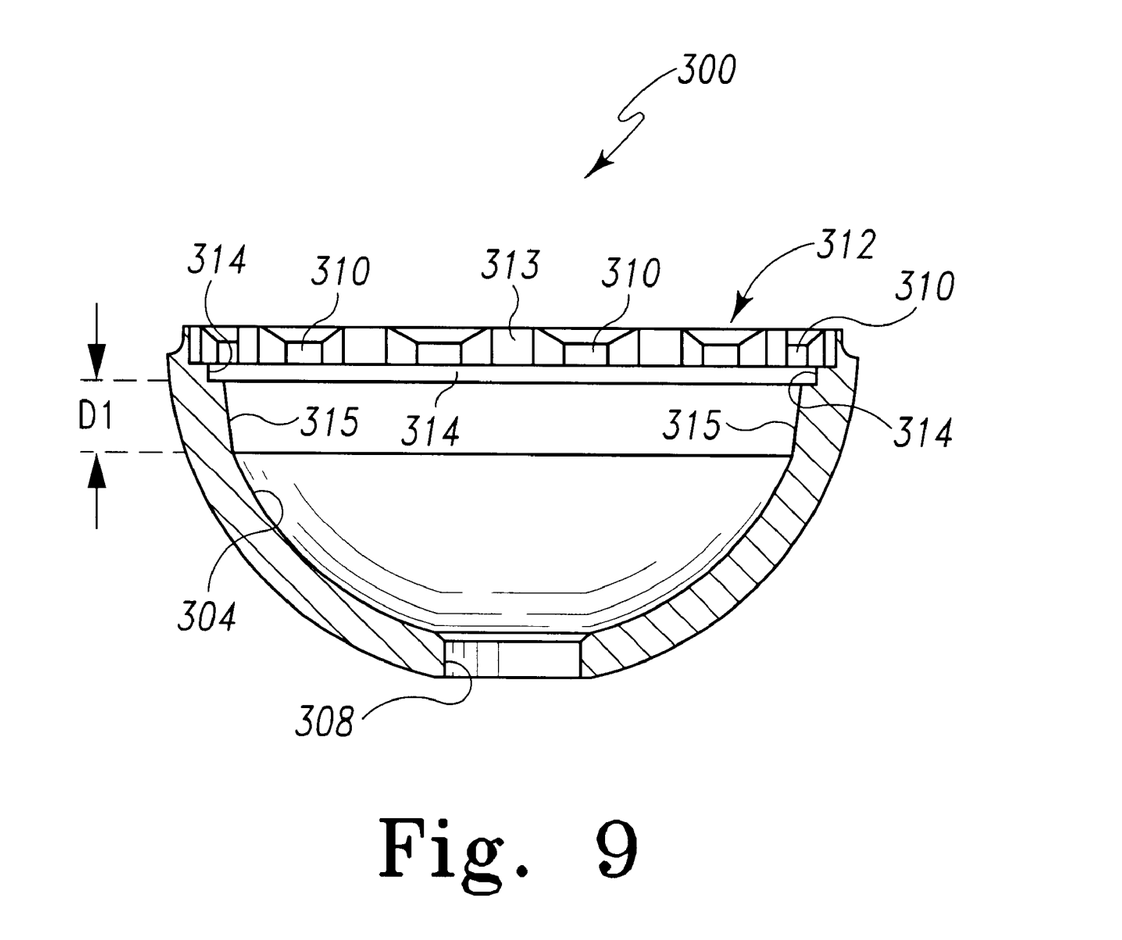
FIG. 9 is a cross-sectional view of the shell of FIG. 8 as viewed in the direction of the arrows 9—9 of FIG. 8.
Figure 10:
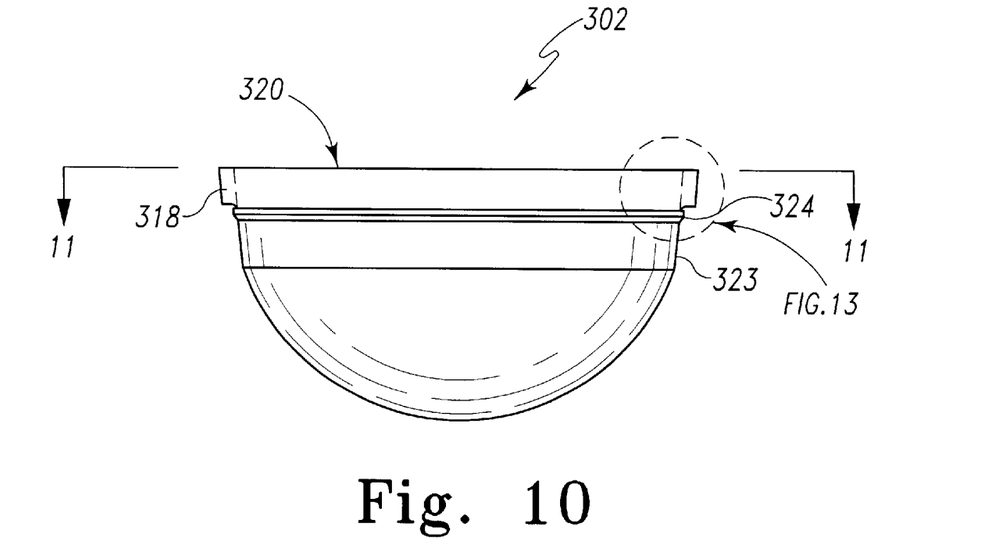
FIG. 10 is an elevational view of a bearing which may be assembled with the shell of FIGS. 7–9 to create an acetabular cup assembly which incorporates the features of the present invention therein.

The shell 300 also includes a female taper 315 which is defined in an inner surface of the shell as shown in FIG. 9. The female taper 315 extends around the entire periphery of the cavity 304 of the shell 300. Moreover, the female taper 315 extends axially for a distance D1 near its upper rim 312 as shown in FIG. 9.

Turning now to FIGS. 10–15, the bearing 302 possesses a generally hemispherical shape and is preferably made from a polymeric material such as ultra high molecular weight polyethylene (UHMWPE). Of course, the bearing 302 could be made of other types of materials which are suitable for implantation into the body of a human being.

Figure 11:
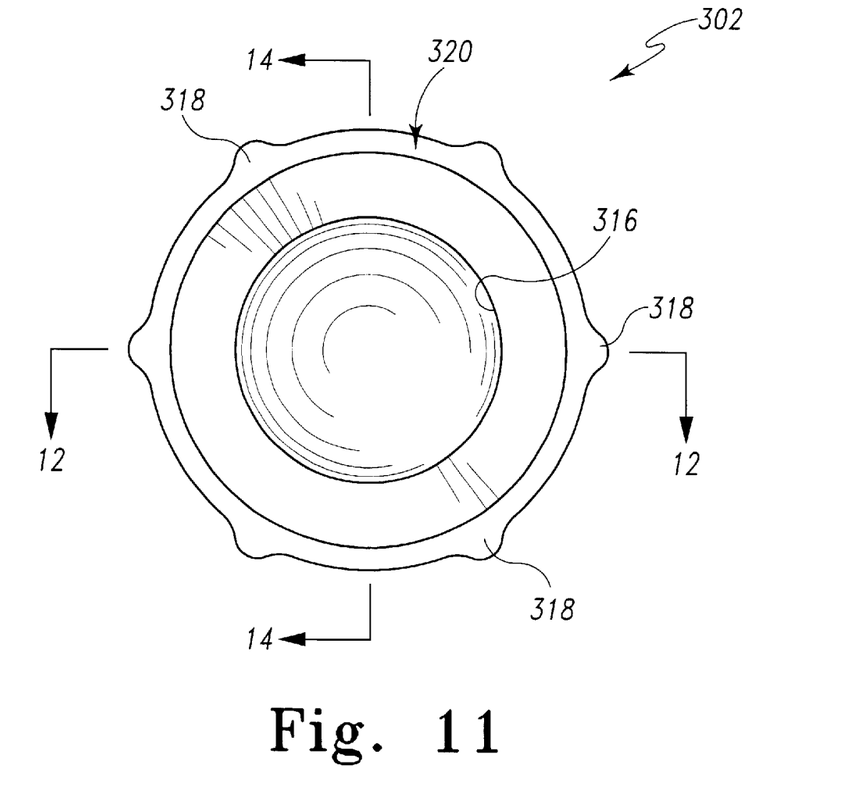
FIG. 11 is an elevational view of the bearing of FIG. 10 as viewed in the direction of the arrows 11—11 of FIG. 10.
Figure 12:
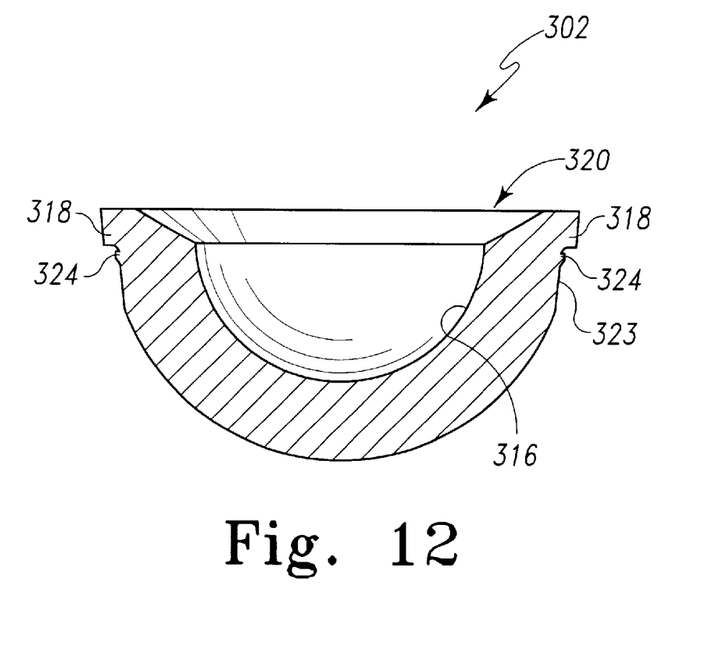
FIG. 12 is a cross-sectional view of the bearing of FIG. 11 as viewed in the direction of the arrows 12—12 of FIG. 11.
Figure 13:
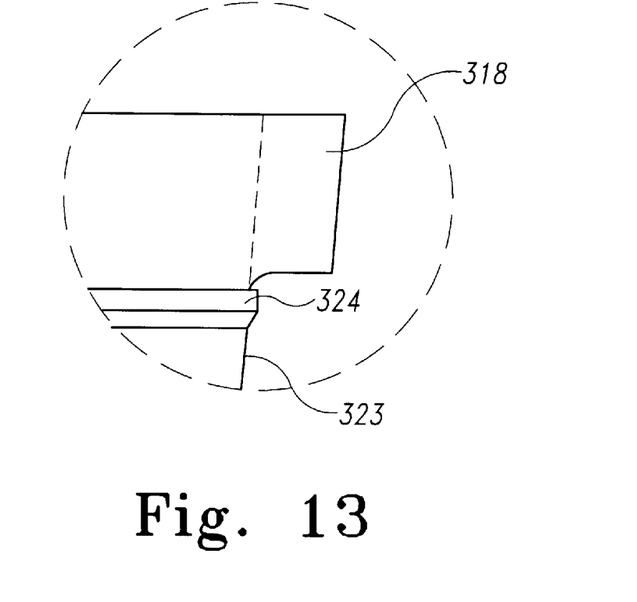
FIG. 13 is an enlarged view of a portion of the bearing of FIG. 10 which is encircled in FIG. 10 and identified as FIG. 13.

The bearing 302 defines a cavity 316 which is configured to receive a prosthetic femoral ball (not shown). The bearing 302 includes a plurality of anti-rotation protrusions 318 which are evenly spaced around an upper rim 320 of the bearing 302 as shown in FIG. 11. Each of the plurality of protrusions 318 extends outwardly away from the center of the bearing 302 as shown in FIG. 11.

Figure 14:
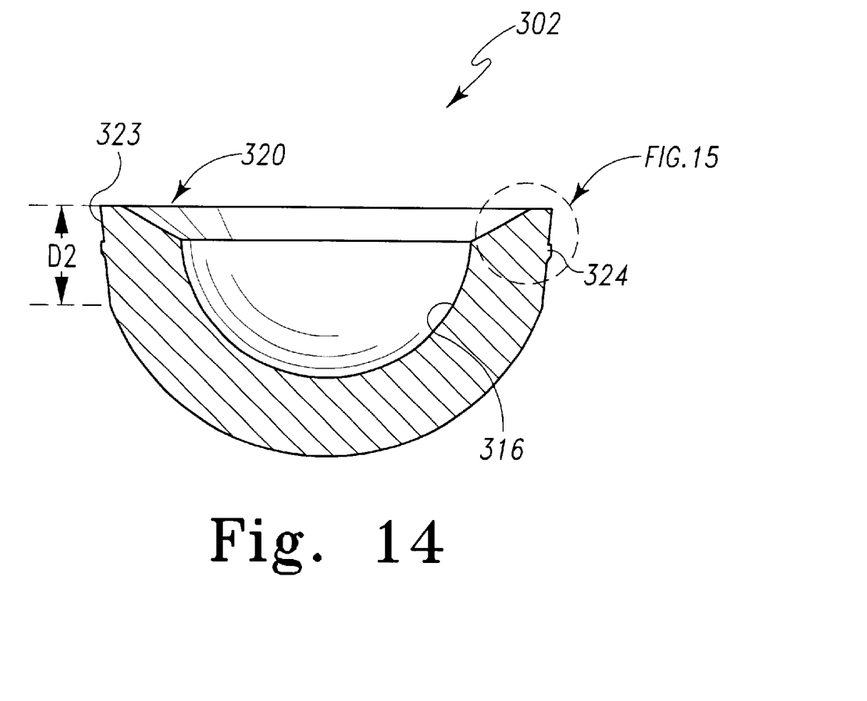
FIG. 14 is a cross-sectional view of the bearing of FIG. 11 as viewed in the direction of the arrows 14—14 of FIG. 11.
Figure 15:
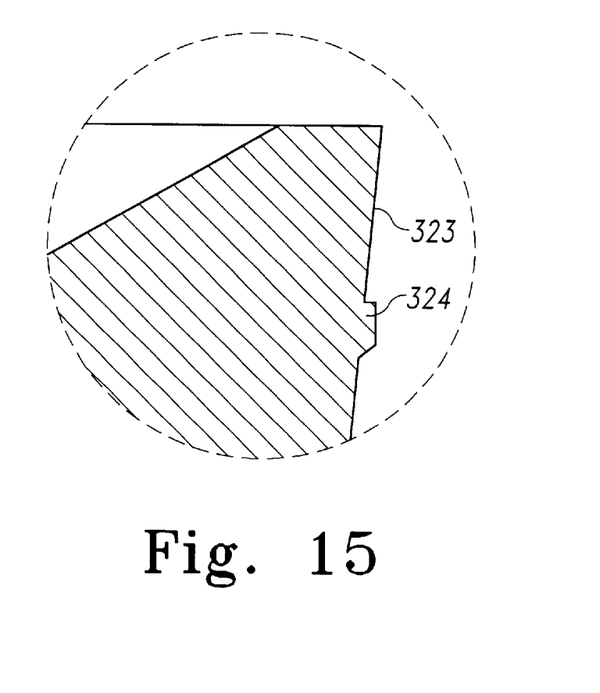
FIG. 15 is an enlarged view of a portion of the bearing of FIG. 14 which is encircled in FIG. 14 and identified as FIG. 15.

The bearing 302 also includes a male taper 323 which is defined in an outer surface of the bearing as shown in FIGS. 10 and 12–15. The male taper 323 extends around the entire periphery of the bearing 302. Moreover, the male taper 323 extends axially for a distance D2 near its upper rim 320 as shown in FIG. 14. The bearing 302 also includes an annular locking member 324 which is located immediately below the plurality of protrusions 318 (see FIGS. 8 and 9). The annular locking member 324 extends around the entire periphery of the bearing 302. The annular locking member 324 extends outwardly from the male taper 323.

When the bearing 302 is positioned in the cavity 304 of the shell 300 after assembly of the acetabular cup assembly made up of the components shown in FIGS. 7–15, the female taper 315 of the shell 300 engages and locks with the male taper 323 of the bearing 302 so as to secure the bearing 302 to the shell 300. Moreover, when the bearing 302 is positioned in the cavity 304 of the shell 300 after assembly of the acetabular cup assembly, the annular locking member 324 of the bearing 302 is located within the annular recess 314 defined in the shell 300 so as to further secure the bearing 302 to the shell 300.

It should be appreciated that the lengths of the female taper 315 and the male taper 323 may vary so long as such lengths are of sufficient magnitude to cause the female taper 315 and the male taper 323 to securely engage each other. Also, in order to achieve appropriate engagement and locking between the female taper 315 of the shell 300 and the male taper 323 of the bearing 302, the taper angle between the two tapers 315, 323 is chosen to be within the range of self-locking tapers. For example, if each taper 315, 323 was in the range of 2°–8.5° (for an aggregate taper angle range of 4°–17°), appropriate engagement and locking between the two components would be achieved.

Moreover, when the bearing 302 is positioned within the cavity 304 of the shell 300 as described above, the plurality of protrusions 318 are respectively positioned within the plurality of recesses 313. With the protrusions 318 positioned within recesses 313, rotational movement of the bearing 302 relative to the shell 300 is inhibited.

FIGS. 16–19 show an alternative bearing 400 which could be substituted for the bearing 302 in order to create yet another acetabular cup assembly which incorporates the features of the present invention therein. Such acetabular cup assembly would cause a cavity 402 of the bearing 400 to be angled with respect to the shell 300 which may be beneficial in certain environments to aid in the prevention of femoral ball dislocation.

Figure 16:
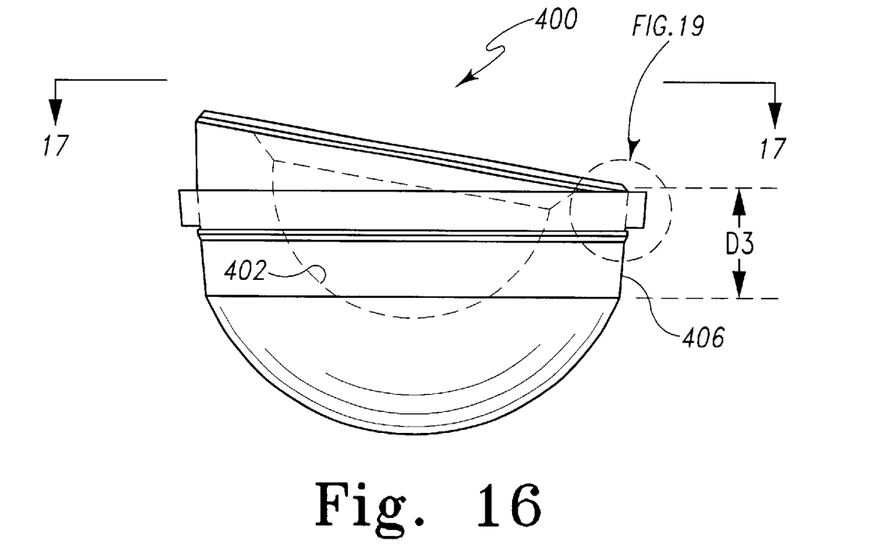
FIG. 16 is an elevational view of alternative bearing which may be assembled with the shell of FIGS. 7–9 to create another acetabular cup assembly which incorporates the features of the present invention therein.
Figure 18:
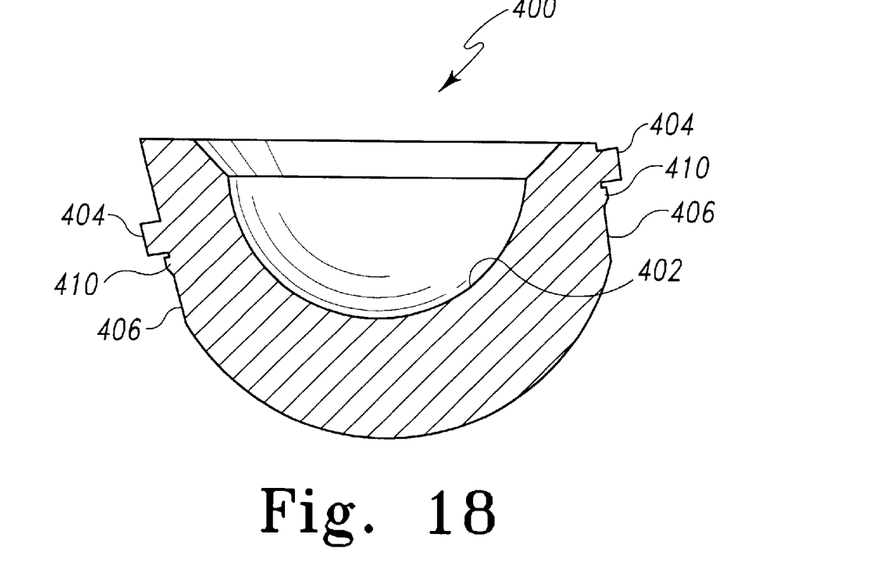
FIG. 18 is a cross-sectional view of the bearing of FIG. 17 as viewed in the direction of the arrows 18—18 of FIG. 17.

The bearing 400 possesses a somewhat hemispherical shape as best shown in FIGS. 16 and 18. The bearing 400 is preferably made from a polymeric material such as ultra high molecular weight polyethylene (UHMWPE). Alternatively, the bearing 400 may be made of other types of materials which are suitable for implantation into the body of a human being such as a metal material or a ceramic material.

Figure 17:
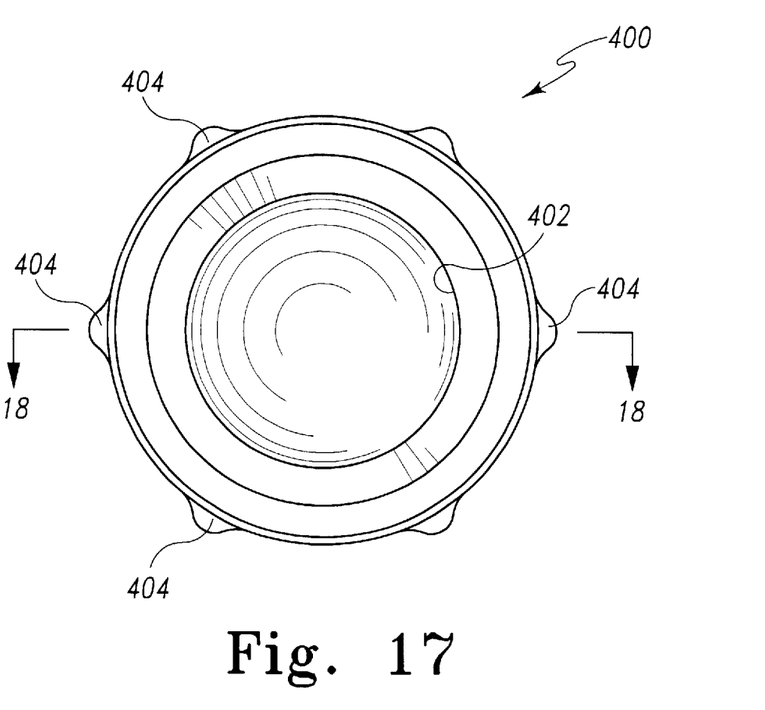
FIG. 17 is an elevational view of the bearing of FIG. 16 as viewed in the direction of the arrows 17—17 of FIG. 16.

The bearing 400 defines the cavity 402 which is configured to receive a prosthetic femoral ball (not shown). The bearing 400 includes a plurality of anti-rotation protrusions 404 which are evenly spaced around the bearing 400 as shown in FIG. 17. Each of the plurality of protrusions 404 extends outwardly away from the center of the bearing 400 as shown in FIG. 17.

Figure 19:
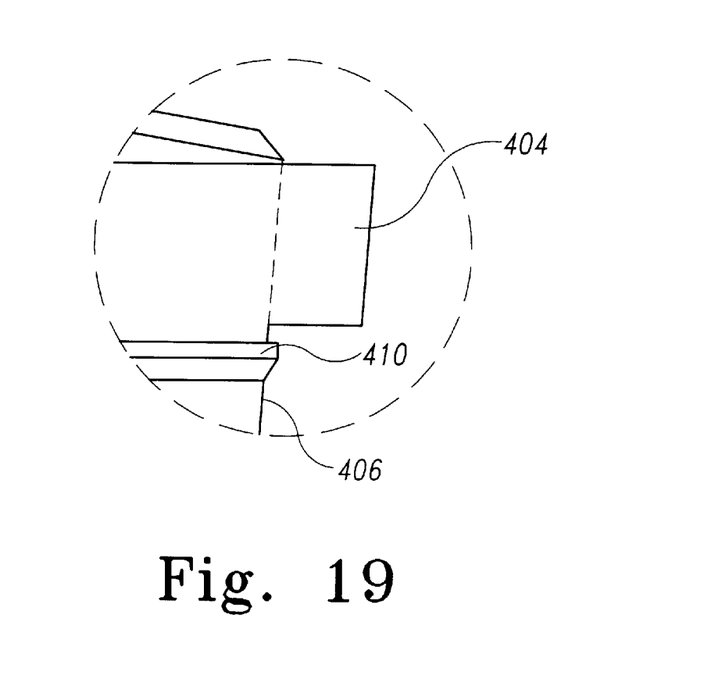
FIG. 19 is an enlarged view of a portion of the bearing of FIG. 16 which is encircled in FIG. 16 and identified as FIG. 19.

The bearing 400 also includes a male taper 406 which is defined in an outer surface of the bearing as shown in FIGS. 16 and 18–19. The male taper 406 extends around the entire periphery of the bearing 400. Moreover, the male taper 406 extends axially for a distance D3 as shown in FIG. 14. The bearing 400 also includes an annular locking member 410 which is located immediately below the plurality of protrusions 404 (see e.g. FIG. 19). The annular locking member 410 extends around the entire periphery of the bearing 400. The annular locking member 410 extends outwardly from the male taper 406.

When the bearing 400 is positioned in the cavity 304 of the shell 300 after assembly of the acetabular cup assembly made up of the components shown in FIGS. 7–9 and 16–19, the female taper 315 of the shell 300 engages and locks with the male taper 406 of the bearing 400 so as to secure the bearing 400 to the shell 300. Moreover, when the bearing 400 is positioned in the cavity 304 of the shell 300 after assembly of the acetabular cup assembly, the annular locking member 410 of the bearing 400 is located within the annular recess 314 defined in the shell 300 so as to further secure the bearing 400 to the shell 300.

It should be appreciated that the lengths of the female taper 315 and the male taper 406 may vary so long as such lengths are of sufficient magnitude to cause the female taper 315 and the male taper 406 to securely engage each other. Also, in order to achieve appropriate engagement and locking between the female taper 315 of the shell 300 and the male taper 406 of the bearing 400, the taper angle between the two tapers 315, 406 is chosen to be within the range of self-locking tapers as described above.

Further, when the bearing 400 is positioned within the cavity 304 of the shell 300 as described above, the plurality of protrusions 404 are respectively positioned within the plurality of recesses 313. With the protrusions 404 positioned within recesses 313, rotational movement of the bearing 404 relative to the shell 300 is inhibited.

Although the invention has been described in detail with reference to certain preferred embodiments, variations and modifications exist within the scope and spirit of the invention as described and defined in the following claims. For example, while the prosthetic cup assembly is disclosed in the context of a hip prosthesis, it has utility in other locations within a patient's body. Also, while the tapers of the various embodiments depicted in the drawings are shown to each be a straight taper, it should be understood that such tapers may assume other configurations such as a curve of a conic section—circle, ellipse, parabola, hyperbola or the like. However, if any such taper takes on a configuration which is non-straight, it should be appreciated that the respective mating taper should take on a complimentary configuration.

What is claimed is:

1. A prosthetic cup assembly, comprising:

a shell defining a shell cavity, said shell including an inner surface configured with (i) a locking recess defined therein, and (ii) a female taper between said locking recess and said shell cavity; and a bearing defining a bearing cavity adapted to receive a prosthetic ball therein, said bearing having an outer surface configured with, and (ii) a locking member extending outwardly therefrom, and (ii) a male taper between said locking member and said bearing cavity, wherein when said bearing is positioned within said shell cavity, (i) said male taper and said female taper engage each other to provide a first connection between said bearing and said shell, and (ii) said locking member is located within said locking recess to provide a second connection between said bearing and said shell.

2. The assembly of claim 1, wherein:

said locking recess extends circumferentially around said inner surface of said shell; and said locking member extends circumferentially around said inner surface of said bearing.

3. The assembly of claim 1, wherein:

said bearing defines an upper bearing rim; and said male taper is positioned adjacent said upper bearing rim.

4. The assembly of claim 1, wherein said male taper and said female taper are self-locking tapers.

5. The assembly of claim 1, wherein:

said shell includes a first number of anti-rotation recesses defined in said inner surface; and said bearing includes a second number of anti-rotation protrusions defined in said outer surface, wherein when said bearing is positioned within said shell cavity, said second number of anti-rotation protrusions are positioned within corresponding ones of said first number of anti-rotation recesses to inhibit relative rotational movement between said bearing and said shell.

6. The assembly of claim 5, wherein said locking recess is interposed between said female taper and said first number of anti-rotation recesses.

7. The assembly of claim 5, wherein:

said shell defines an upper shell rim; and said first number of recesses is positioned adjacent said upper bearing rim.

8. The assembly of claim 5, wherein said first number is greater than said second number.

9. A prosthetic cup assembly, comprising:

a shell defining a shell cavity, said shell including an inner surface configured with (i) a first number of anti-rotation recesses defined therein, and (ii) a female taper between said anti-rotation recesses and said shell cavity; and a bearing defining a bearing cavity adapted to receive a prosthetic ball therein, said bearing having an outer surface configured with, and (ii) a second number of anti-rotation protrusions, and (ii) a male taper between said anti-rotation protrusions and said bearing cavity, wherein when said bearing is positioned within said shell cavity, (i) said male taper and said female taper engage each other to provide a first connection between said bearing and said shell, and (ii) said second number of anti-rotation protrusions are positioned within corresponding ones of said first number of anti-rotation recesses to provide a second connection between said bearing and said shell.

10. The assembly of claim 9, wherein said first number is greater than said second number.

11. The assembly of claim 10, wherein:

said first number of anti-rotation recesses includes twelve recesses; and said second number of anti-rotation protrusions includes six protrusions.

12. The assembly of claim 9, wherein:

said shell includes a locking recess defined in said inner surface thereof between said first number of anti-rotation recesses and said female taper; and said bearing includes a locking member defined in said outer surface thereof configured to be positioned within said locking recess to provide a third connection between said bearing and said shell.

13. The assembly of claim 12, wherein:

said locking recess extends circumferentially around said inner surface of said shell; and said locking member extends circumferentially around said inner surface of said bearing.

14. A prosthetic cup assembly, comprising:

a shell defining a shell cavity, said shell including an inner surface configured with (i) a first number of anti-rotation recesses defined therein, and (ii) a locking recess disposed between said anti-rotation recesses and said shell cavity and a bearing defining a bearing cavity adapted to receive a prosthetic ball therein, said bearing having an outer surface configured with, and (ii) a second number of anti-rotation protrusions, and (ii) a locking member disposed between said anti-rotation protrusions and said bearing cavity, wherein when said bearing is positioned within said shell cavity, (i) said locking member is positioned within said locking recess to provide a first connection between said bearing and said shell, and (ii) said second number of anti-rotation protrusions are positioned within corresponding ones of said first number of anti-rotation recesses to provide a second connection between said bearing and said shell.

15. The assembly of claim 14, wherein:

said locking recess extends circumferentially around said inner surface of said shell; and said locking member extends circumferentially around said inner surface of said bearing.

* * * * *